United States Patent [19]

Horstmann et al.

[11] Patent Number: 5,053,421

[45] Date of Patent: Oct. 1, 1991

[54] DI-STYRL-PHENYL-TRIGLYCOL ETHER AS CRYSTALLIZATION INHIBITOR

[75] Inventors: Heinz-Otto Horstmann, Bergisch-Gladbach; Ulrich Engelhardt, Leverkusen; Karl Reizlein, Cologne; Rolf-Jürgen Singer, Wuppertal; Klaus Wangermann, Krefeld; Wolfgang Wirth, Hennef; Frank Bartkowiak, Cologne; Günther Boehmke, Leverkusen; Hans Schulze, Cologne, all of Fed. Rep. of Germany

[73] Assignee: Bayer Aktiengesellschaft, Leverkusen, Fed. Rep. of Germany

[21] Appl. No.: 501,692

[22] Filed: Mar. 29, 1990

[30] Foreign Application Priority Data

Apr. 5, 1989 [DE] Fed. Rep. of Germany ....... 3910922

[51] Int. Cl.$^5$ .................... A01N 43/64; C07D 249/14

[52] U.S. Cl. .................................. 514/383; 514/971; 548/267.8; 548/268.6

[58] Field of Search .............................. 514/971, 383; 548/267.8, 268.6

[56] References Cited

U.S. PATENT DOCUMENTS

| | | | |
|---|---|---|---|
| 3,952,002 | 4/1976 | Kramer et al. | 260/308 R |
| 4,348,385 | 9/1982 | Synek | 424/173 |
| 4,723,984 | 2/1988 | Holmwood et al. | 7/76 |
| 4,943,299 | 7/1990 | Schulze et al. | 8/610 |

FOREIGN PATENT DOCUMENTS

| | | |
|---|---|---|
| 0040345 | 11/1981 | European Pat. Off. . |
| 0102003 | 3/1984 | European Pat. Off. . |
| 2324010 | 1/1975 | Fed. Rep. of Germany . |

*Primary Examiner*—Allen J. Robinson

*Attorney, Agent, or Firm*—Sprung Horn Kramer & Woods

[57] ABSTRACT

In the spraying of an aqueous liquor comprising at least one of 1-(4-chlorophenyl)-4,4-dimethyl-3-(1,2,4-triazol-1-yl-methyl)-pentan-3-ol and 1-(4-chlorophenoxy)-3,3-dimethyl-1-(1,2,4-triazol-1-yl)-butan-2-ol, the improvement which comprises including in the liquor di-styryl-phenyl-tri-glycol ether, whereby crystallization of II and III is reduced.

2 Claims, 1 Drawing Sheet

DI-STYRL-PHENYL-TRIGLYCOL ETHER AS CRYSTALLIZATION INHIBITOR

The present invention relates to the new use of di-styryl-phenyl-triglycol ether for prevention of crystallization on application of aqueous spray liquors based on certain fungicidal active compounds.

Spray apparatuses which are usually employed for applying aqueous formulations of plant treatment agents contain several filters and nozzles. Thus, for example, there are suction filters between suction component and tank pump, and furthermore pressure filters, which are positioned in the pressure region after the pump. In addition, the apparatuses may also contain nozzle filters directly before the spray nozzles. All of these filters and also the nozzles can be blocked more or less easily by active compound crystallizing out during application of aqueous spray liquors based on solid active compounds.

It has already been disclosed that 1-(4-chlorophenyl)-4,4-dimethyl-3-(1,2,4-triazol-1-yl-methyl)-pentan-3-ol and 1-(4-chlorophenoxy)-3,3-dimethyl-1-(1,2,4-triazol-1-yl)-butan-2-ol have a fungicidal action and can be applied in the form of aqueous spray liquors to plants and/or their environment (compare European Offenlegungsschrift (European Published Specification) 0,040,345 and German Patent Specification 2,324,010). Surface-active substances, such as, for example, alkylaryl polyglycol ethers, can be employed for the preparation of such spray liquors. However, the disadvantage of using these conventional formulations is that the active compounds tend to crystallize and can block both the filters and the nozzles of the spray apparatuses.

It has now been found that di-styrylphenyl-triglycol ether of the formula

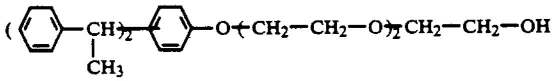

(I)

can be used, during application of aqueous spray liquors containing

A) 1-(4-chlorophenyl)-4,4-dimethyl-3-(1,2,4-triazol-1-yl-methyl)-pentan-3-ol of the formula

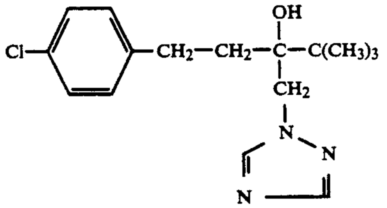

(II)

and/or 1-(4-chlorophenoxy)-3,3-dimethyl-1-(1,2,4-triazol-1-yl)-butan-2-ol of the formula

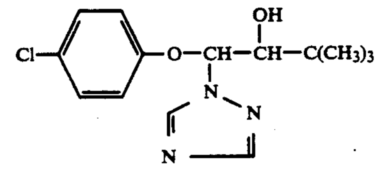

(III)

and

B) if appropriate one or more other active compounds and additives, to prevent crystallization of the active compounds of the formulae (II) and/or (III).

It is to be described as exceptionally surprising that the tendency of 1-(4-chlorophenyl)-4,4-dimethyl-3-(1,2,4-triazol-1-yl-methyl)-pentan-3-ol and 1-(4-chlorophenoxy)-3,3-dimethyl-1-(1,2,4-triazol-1-yl)-butan-2-ol to crystallize can be greatly reduced by the use according to the invention of di-styryl-phenyl-tri-glycol ether of the formula (I). Above all, it was not to be expected that di-styryl-phenyl-tri-glycol ether of the formula (I) is considerably more suitable for the stated purpose than other substances of comparable action.

The use of di-styryl-phenyl-tri-glycol ether of the formula (I) in aqueous formulations based on the fungicidal active compounds of the formulae (II) and/or (III) has a number of advantages. Thus, di-styryl-phenyl-tri-glycol ether of the formula (I) is a substance which can be handled without problems and is also available in relatively large amounts. The use of the substance of the formula (I) furthermore prevents blockage both of the filters and of the nozzles of the spray apparatuses during spraying of aqueous formulations containing active compounds of the formulae (II) and/or (III). It is also advantageous that di-styryl-phenyl-tri-glycol ether of the formula (I) has no undesirable side effects at all when used in plant protection.

Di-styryl-phenyl-tri-glycol ether of the formula (I) and its use as an auxiliary for dyeing textiles are already known (compare DE-OS (German Published Specification) 3,734,159). The compound can be prepared by reacting di-styryl-phenol with ethylene oxide in the presence of potassium hydroxide.

The active compounds of the formulae (II) and (III) and their use for combating phytopathogenic fungi are likewise known (compare EP-OS (European Published Specification) 0,040,345 and German Patent Specification 2,324,010). The active compounds can be employed in the customary formulations here. They are preferably applied in the form of aqueous spray liquors.

In addition to the active compounds of the formulae (II) and (III), the spray liquors which can be used according to the invention can also contain one or more other active compounds. Compounds which are preferably suitable here are those with fungicidal properties. Examples which may be mentioned of such active compounds which can additionally be used are:

1-(4-chlorophenoxy)-3,3-dimethyl-(1,2,4-triazol-1-yl)-butan-2-one (triadimefon),
1-(4-phenyl-phenoxy)-3,3-dimethyl-(1,2,4-triazol-1-yl-butan-2-ol (bitertanol),
N,N-dimethyl-N'-phenyl-(N'-fluorodichloro-methylthio)-sulphamide (dichlofluanid),
N,N-dimethyl-(N,-fluorodichloronethylthio)-N'-(4-methylphenyl)-sulphamide (tolylfluanid),
N-trichloromethylmercapto-4-cyclohexene-1,2-dicarboxamide (captan),
N-(1,1,2,2-tetrachloroethyl-sulphenyl)-cis-4-cyclohexene1,2-dicarboxamide (captafol),
N-trichloromethylthio-phthalimide (folpet),
n-dodecyl-guanidine acetate (dodine),
tetrachloro-isophthalo-dinitrile (chlorothalonil),
4,5,6,7-tetrachlorophthalide,
zinc ethylene-bis-dithiocarbamate (zineb),
manganese ethylene-bis-dithiocarbamate (maneb),
zincethylene-bis-dithiocarbamate/manganeseethylene-bisdithiocarbamate (mancozeb), zinc propylene-1,2-bis-dithiocarbamate (propineb),
1-[3-(4-(1,1-dimethylethyl)-phenyl)-2-methylpropyl]-piperidine (fenpropidin),
N-tridecyl-2,6-dimethyl-morpholine (tridemorph),
2-[2-(2,4-dichlorophenyl)-2-(2-propenyloxy)-ethyl-]imidazole (imazalil).
N-[2-(2,4,6-trichlorophenoxy)-ethyl]-N-propyl-1H-imidazole (prochloraz),
1,2-dimethyl-cyclopropane-1,2-dicarboxylic acid 3,5-dichlorophen-ylimide (procymidone),
2-methoxycarbamoyl-benzimidazole (carbendazim), methyl 1-(but-vlcarbamoyl)-2-benzimidazole-carbamate (benomyl),
2,4-dichloro-6-(2′-chlorophenyl-amino)-1,3,5-triazine (anilazine),
bis-(8-guanidine-O-octyl)-amine triacetate (guazatine), and
1-(4-chlorobenzyl)-1-cyclopentyl-3-phenyl-urea (pencyron).

Possible additives which can be present in the spray liquors which can be used according to the invention are surface-active substances, organic diluents, low temperature stabilizers and adhesives.

Possible surface-active substances here are nonionic and anionic emulsifiers, such as polyoxyethylene fatty acid esters, polyoxyethylene fatty alcohol ethers, alkylaryl polyglycol ethers, alkylsulphonates, alkylsulphates and arylsulphonates. The enulsifiers can be employed here individually or as a mixture. Preferred emulsifiers which may be mentioned are:
polyox.yethylene sorbitan monolaurate having on average 20 oxyethylene units per molecule,
polyoxyethylene sorbitan monopalmitate having on average 20 oxyethylene units per molecule,
polyoxyethylene sorbitan monostearate having on average 20 oxyethylene units per molecule,
sorbitan monolaurate,
sorbitan monopalmitate,
sorbitan monostearate,
polyoxyethylene oleyl ether having on average 10 oxyethylene units per molecule,
polyoxyethylene oleyl ether having on average 20 oxyethylene units per molecule,
bis-[α-methyl-(4-methyl-benzyl)]-phenyl-polyglycol ether having on average 27 oxyethylene units per molecule,
bis-[α-methyl-(4-n-dodecyl-benzyl)]-phenyl-polyglycol ether having on average 27 oxyethylene units per molecule,
bis-(4-methyl-benzyl)-phenyl-polyglycol ether having on average 27 oxyethylene units per molecule,
bis-(4-n-dodecyl-benzyl)-phenyl-polyglycol ether having on average 27 oxyethylene units per molecule,
tris-[α-methyl-(4-methyl-benzyl)]-phenyl-polyglycol ether having on average 17 oxyethylene units per molecule, nonylphenol-polyglycol ether having on average 15 oxyethylene units per molecule,
nonylphenol-diglycol ether having on average 2 oxyethylene
units per molecule,
n-dodecyl sodium sulphonate,
sodium lauryl sulphate,
sodium 4-(n-nonyl)phenyl-sulphonate,
sodium 4-(tetrapropylene)-phenyl-sulphonate,
ammonium 4-(i-dodecyl)-phenyl-sulphonate,
calcium 4-(i-dodecyl)-phenyl-sulphonate,
2-hydroxyethyl)-ammonium 4-(n-dodecyl)-phenyl-sulphonate,
bis-(2-hydroxymethyl)-ammonium 4-(n-dodecyl)-phenyl-sulphonate,
tris-(2hydroxymethyl)-ammonium 4-(n-dodecyl)-phenyl-sulphonate, and
calcium 4-(n-dodecyl)-phenyl-sulphonate.

The emulsifiers used in practice from the group of alkylaryl, polyglycol ethers are in general mixtures of several compounds. They are in particular mixtures of substances which differ in the degree of substitution on the phenyl ring bonded to the oxyethylene unit and the number of oxyethylene units. Fractions can also be calculated from these as mean values for the number of substituents on the phenyl ring. Examples which may be mentioned are substances for which the following average compositions result:

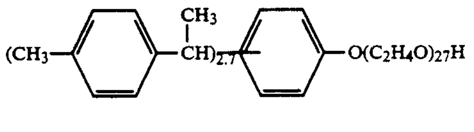

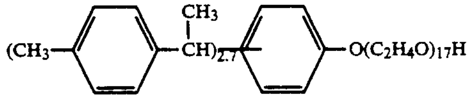

Organic diluents which can be present in the spray liquors which can be used according to the invention are all the polar and non-polar organic solvents which can be customarily employed for such purposes. Preferred possible solvents are ketones, such as methyl isobutyl ketone and cyclohexanone, and furthermore amides, such as dimethylformamide, and moreover cyclic compounds, such as N-methyl-pyrrolidone and butyrolactone, and moreover strongly polar solvents, such as dimethyl sulphoxide, and furthermore aromatic hydrocarbons, such as xylene, and in addition esters, such as propylene glycol monomethyl ether-acetate, dibutyl adipate, hexyl acetate, heptyl acetate, tri-n-butyl citrate and di-n-butyl phthalate, and furthermore alcohols, such as ethanol, n- and i-propanol, n- and i-butanol, n- and i-amyl alcohol, benzyl alcohol and 1-methoxy-2-propanol.

Low temperature stabilizers which the spray liquors which can be used according to the invention can contain are all the substances usually suitable for this purpose. Preferred possible substances are urea, glycerol and propylene glycol.

Adhesives which can be employed in the spray liquors which can be used according to the invention are all the substances which are usually suitable for this purpose. Preferred possible substances are adhesives such as carboxymethylcellulose, naturally occurring and synthetic pulverulent, granular or latex polymers, such as gum arabic, polyvinyl alcohol and polyvinyl acetate, and naturally occurring phospholipids, such as cephalins and lecithins, and also synthetic phospholipids. Further additives can be mineral and vegetable oils.

Water is moreover in each case present in the spray liquors which can be used according to the invention.

The active compound concentrations in the spray liquors which can be used according to the invention can be varied within a certain range. The active compound concentrations are in general between 0.0001 and 2 per cent by weight, preferably between 0.001 and 1.5 per cent by weight.

The ratio of active compound to di-styryl-phenyl-tri-glycol ether of the formula (I) can also be varied within a certain range. The weight ratio of active compound from group (A) to di-styryl-phenyl-tri-glycol ether of the formula (I) is in general between 1:0.2 and 1:5, preferably between 1:0.25 and 1:1.0.

The amounts of other active compounds or additives in the spray liquors which can be used according to the invention can be varied within a substantial range. They are of an order of magnitude such as is usually the case in such aqueous spray liquors.

The spray liquors which can be used according to the invention are prepared by customary methods. In general, a procedure is followed in which a concentrate is first prepared by bringing together the required components in any desired sequence and mixing them homogeneously at temperatures between 15° and 30° C. and if appropriate filtering the mixture formed. To prepare the ready-to-use spray liquors, the concentrated formulation is mixed with the particular desired amount of water, if appropriate with stirring and/or pumping, so that the formulation is uniformly distributed in the water as a fine dispersion.

It is also possible to add the di-styryl-phenyl-tri-glycol ether of the formula (I) when the concentrate is diluted with water to give the ready-to-use spray liquor.

It is possible to use, both for preparation of the concentrated formulations and for preparation and application of the spray liquors which can be used according to the invention, all the mixing apparatuses and spray apparatuses usually suitable for this purpose.

By using di-styryl-phenyl-tri-glycol ether of the formula (I) in aqueous spray liquors based on active compounds of the formulae (II) and /or (III), crystallization of active compound both in the concentrated commercially available formulation and in the filters and discharge openings of the spray apparatuses during application of the aqueous spray liquors prepared therefrom is either completely suppressed or prevented to the extent that application of the spray liquors is not impaired.

The invention will also be desired with reference to the accompanying drawing, wherein FIG. 1 is a photomicrograph showing crystal deposit in accordance with the prior art; and FIG. 2 is a photomicrograph showing reduced crystal deposit in accordance with the invention.

The preparation and crystallization properties of the spray liquors which can be used according to the invention are illustrated by the examples which follow.

PREPARATION EXAMPLES

EXAMPLE 1

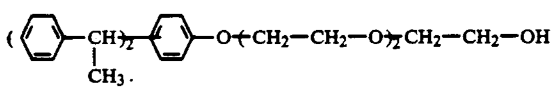

(I)

A mixture of 151 parts by weight of di-styrylphenol and 2 parts by weight of solid potassium hydroxide is heated at 110° C., with stirring. The reaction mixture is kept at this temperature and nitrogen is passed through under reduced pressure in order to drive off the water formed. 66 parts by weight of ethylene oxide are then passed in at temperatures between 140° C. and 155° C. under a pressure of 2 bar, with stirring. The mixture is stirred for a further 2 hours under the autogenous pressure, the mixture is then allowed to cool to 80° C., and 2.3 parts by weight of acetic acid are added. Di-styryl-phenyl-tri-glycol ether are obtained in this manner in the form of a viscous yellowish liquid of solidification point −10° C.

Density: 1.076 g/cm$^3$ at 20° C.

Refractive index: $n^{40}_D = 1.5572$

EXAMPLE 2

To prepare a formulation, 23.8 parts by weight of 1-(4-chlorophenyl)-4,4-dimethyl-3-(1,2,4-triazol-1-yl-methyl)-pentan-3-ol of the formula

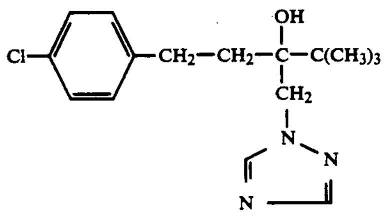

(II)

20.0 parts by weight of di-styryl-phenyl-triglycol ether of the formula

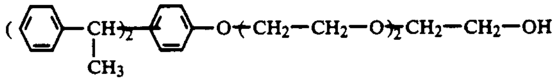

(I)

15.0 parts by weight of the emulsifier of the average composition of the formula

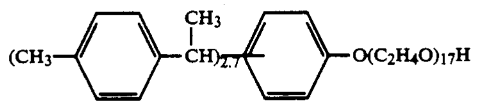

5.0 parts by wight of the emulsifier of the average composition of the formula

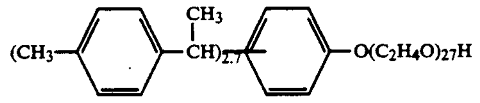

and 36.2 parts by weight of dimethylformamide are mixed at room temperature and stirred to give a homogeneous liquid. A spray liquor containing the concentrate in a concentration of 1% by weight is prepared from the resulting concentrate by mixing with water.

EXAMPLE 3

To prepare a formulation, 25.0 parts by weight of 1-(4-chlorophenyl)-4,4-dimethyl-3-(1,2,4-triazol-1-yl-methyl)-pentan-3-ol of the formula

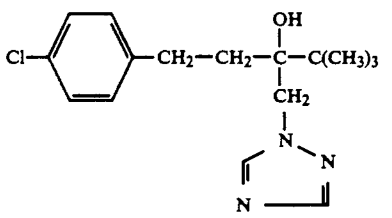

(II)

12.5 parts by weight of 1-(4-chlorophenoxy)-3,3-diemthyl-1-(1,2,4-triazol-1-yl)-butan-2-ol of the formula

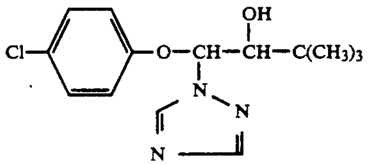

(III)

20.0 parts by weight of the emulsifier of the average composition of the formula

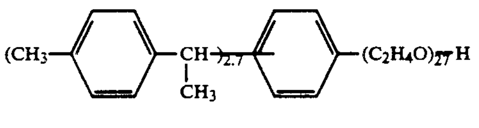

10.0 parts by weight of di-styryl-phenyl-triglycol ether of the formula

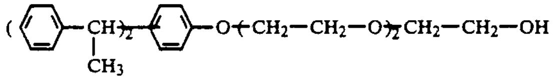

(I)

and 32.5 parts by weight of dimethylformamide are mixed at room temperature and stirred to give homogeneous liquid. A spray liquor containing the concentrate in a concentration of 1% by weight is prepared from the resulting concentrate by mixing with water.

EXAMPLE 4

To prepare a formulation, 12.1 parts by weight of 1-(4-chlorophenyl)-4,4-dimethyl-3-(1,2,4,-triazol-1-yl-methyl)-pentan-3-ol of the formula

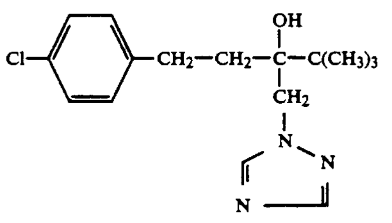

(II)

9.7 parts by weight of 1-(4-chlorophenoxy)-3,3-dimethyl-1-(1,2,4-trizol-1-yl)-butan-2-one of the formula

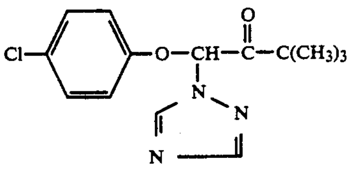

10.0 parts by weight of di-styryl-phenyl-triglycol ether of the formula

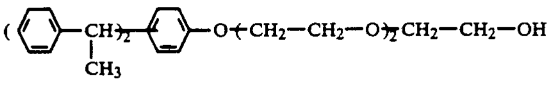

(I)

20.0 parts by weight of the emulsifier of the average composition of the formula

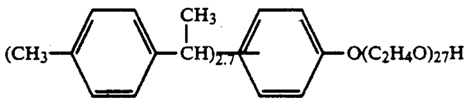

and 48.2 parts by weight of dimethylformamide are mixed at room temperature and stirred to give a homogeneous liquid. A spray liquor containing the concentrate in a concentration of 1% by weight is prepared from the resulting concentrate by mixing with water.

Comparison Example A

To prepare a formulation, 24.5 parts by weight of 1-(4-chlorophenyl)-4,4-dimethyl-3-(1,2,4-triazol-1-yl-methyl)-pentan-3-ol of the formula

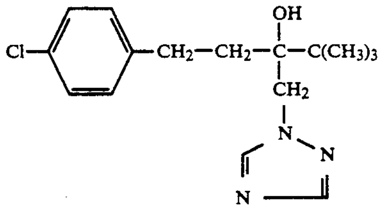

(II)

20.0 parts by weight of a mixture consisting of equal parts of (2-hydroxyethyl)-ammonium 4-(n-dodecyl)-phenylsulphonate and the emulsifier of the average composition of the formula

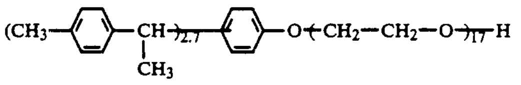

and 55.5 parts by weight of dimethylformamide are mixed at room temperature and stirred to give a homogeneous liquid.. A spray liquor containing the concentrate in a concentration of 1% by weight is prepared from the resulting concentrate by mixing with water.

Comparison Example B

To prepare a formulation, 25.0 parts by weight of 1-(4-chlorophenyl)-4,4-dimethyl-3-(1,2,4-triazol-1-yl-methyl)-pentan-3-ol of the formula

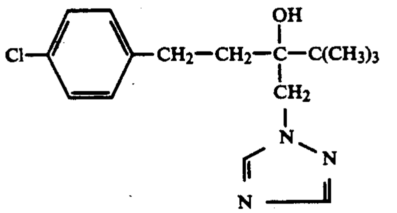

(II)

12.5 parts by weight of 1-(4-chlorophenoxy)-3,3-dimethyl-1-(1,2,4-triazol-1-yl)-butan-2-ol of the formula

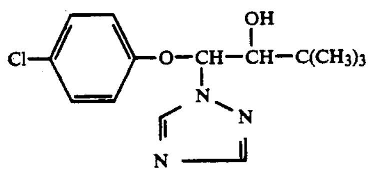

(III)

20.0 parts by weight of a mixture consisting of equal parts of (2-hydroxyethyl)-ammonium 4-(n-dodecyl)-phenyl-sulphonate and the emulsifier of the average composition of the formula

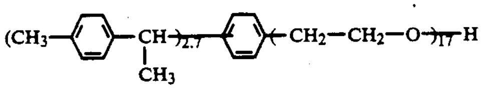

and 42.5 parts by weight of dimethylformamide are mixed at room temperature and stirred to give a homogeneous liquid. A spray liquor containing the concentrate in a concentration of 1% by weight is obtained from the resulting concentrate by mixing with water.

Use Example I

To test the crystallization properties, 1% strength spray liquors are in each case shaken by machine at room temperature. After the times stated in the tables which follow, the amount of crystals which have separated out is in each case determined and expressed as a percentage of the total amount of active compound present in the particular spray liquor.

The experimental results can be seen from the tables which follow.

TABLE I-a

| Spray liquor according to | Shaking time in hours | Amount of crystals deposited in % >150 μm | >1.2 μm | Total |
|---|---|---|---|---|
| (A) known | 2 | 12 | 14 | 26 |
| (2) | 2 | <1 | 2 | 3 |
| (4) | 2 | 1.4 | 0.9 | 2.3 |

TABLE I-b

| Spray liquor according to Example | Shaking time in hours | Amount of crystals deposited in % >150 μm | >1.2 μm | Total |
|---|---|---|---|---|
| (B) known | 6 | 5 | 10 | 15 |
| (3) | 6 | <1 | 3 | 4 |

Example II

To test the crystallization properties, in each case 250 ml of a spray liquor having a concentrate content of 1% by weight are pumped in circulation through a fine-meshed sieve in a flow-through apparatus for 15 minutes with the aid of a pump. After this operation has been repeated eight times with 250 ml of freshly employed spray liquor each time, the crystal deposit on the sieve is photographed.

The corresponding photographs are shown in FIGS. 1 and 2.

Figure 1:
FIG. 1 shows, in 25-fold magnification, the crystal deposit formed on the sieve on pumping through eight 250 ml batches of the spray liquor according to Example (A).
Figure 2:
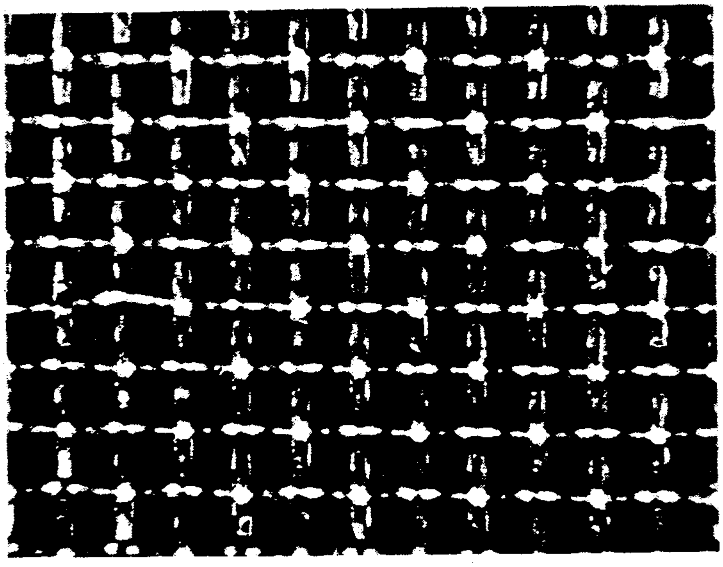
FIG. 2 shows, in 25-fold magnification, the crystal deposit formed on the sieve on pumping through eight 250 ml batches of the spray liquor according to Example (2).

The figures show that the screen is almost completely blocked in the case of the known spray liquor according to Example (A), whereas in the case of the spray liquor according to Example (2) no crystal deposit is observed.

It is understood that the specification and examples are illustrative but not limitative of the present invention and that other embodiments within the spirit and scope of the invention will suggest themselves to those skilled in the art.

What is claimed is:

1. An aqueous spray liquor composition comprising a) at least one component selected from the group consisting of 1-(4-chlorophenyl)-4,4-di-methyl-3-(1,2,4-triazol-1-yl-methyl)-pentan-3-ol of the formula

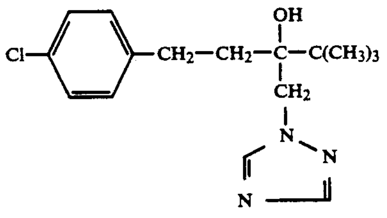

(II)

and 1-(4-chlorophenoxy)-3,3-dimethyl-1-(1,2,4-triazol-1-yl)-butan-2-ol of the formula

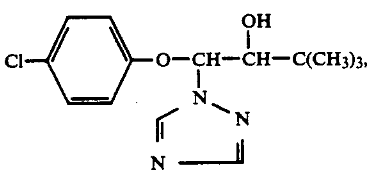

(III)

and (b) di-styryl-phenyl-tri-glycol ether of the formula

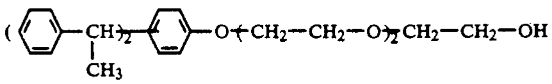

(I)

wherein the active compounds II plus III are present in about 0.0001 to 2 per cent by weight and the ratio of compounds II plus III:I is from about 1:0.2 to 1:5.

2. A method of controlling crystal growth in an aqueous spray liquor comprising at least one component selected from the group consisting of 1-(4-chlorophenyl)-4,4-dimethyl-3-(1,2,4-triazol-1-yl-methyl)-pentan-3-ol and 1-(4-chlorophenoxy)-3,3-dimethyl-1-(1,2,4-triazol-1 -yl)-butan-2-ol, comprising adding to the aqueous spray liquor an effective amount of di-styryl-phenyl-tri-glycol ether, whereby crystallization is reduced.

* * * * *